United States Patent
Malewicz

(10) Patent No.: US 8,764,745 B2
(45) Date of Patent: Jul. 1, 2014

(54) CRYOPROBE CLAMP HAVING TRANSMURALITY ASSESSMENT WINDOW

(75) Inventor: Andrzej M. Malewicz, Minneapolis, MN (US)

(73) Assignee: Medtronic ATS Medical, Inc., Plymouth, MN (US)

( * ) Notice: Subject to any disclaimer, the term of this patent is extended or adjusted under 35 U.S.C. 154(b) by 714 days.

(21) Appl. No.: 12/864,198

(22) PCT Filed: Jan. 26, 2009

(86) PCT No.: PCT/US2009/032014
§ 371 (c)(1),
(2), (4) Date: Jul. 22, 2010

(87) PCT Pub. No.: WO2009/094640
PCT Pub. Date: Jul. 30, 2009

(65) Prior Publication Data
US 2010/0298819 A1     Nov. 25, 2010

Related U.S. Application Data

(60) Provisional application No. PCT/US2009/032014, filed on Jan. 26, 2009, provisional application No. 61/023,735, filed on Jan. 25, 2008.

(51) Int. Cl.
| | | |
|---|---|---|
| *A61B 18/12* | (2006.01) | |
| *A61B 18/02* | (2006.01) | |
| *A61B 17/28* | (2006.01) | |
| *A61B 18/00* | (2006.01) | |
| *A61B 17/29* | (2006.01) | |

(52) U.S. Cl.
CPC .......... *A61B 18/02* (2013.01); *A61B 2018/025* (2013.01); *A61B 2018/0225* (2013.01); *A61B 2017/2808* (2013.01); *A61B 2018/00351* (2013.01); *A61B 2017/2944* (2013.01); *A61B 18/0218* (2013.01); *A61B 2018/0256* (2013.01)
USPC ............................................ 606/41; 128/898

(58) Field of Classification Search
USPC ....................................................... 606/1–52
See application file for complete search history.

(56) References Cited

U.S. PATENT DOCUMENTS

| | | |
|---|---|---|
| 2,677,117 A | 4/1952 | Swain |
| 6,277,117 B1 * | 8/2001 | Tetzlaff et al. .................. 606/48 |
| 6,394,949 B1 | 5/2002 | Crowley et al. |
| 8,262,649 B2 * | 9/2012 | Francischelli .................. 606/23 |
| 2002/0161364 A1 | 10/2002 | Mulier et al. |
| 2003/0060685 A1 | 3/2003 | Houser et al. |

(Continued)

FOREIGN PATENT DOCUMENTS

| | | |
|---|---|---|
| GB | 1 413 282 A | 11/1975 |
| WO | WO2004/086490 | 10/2004 |

*Primary Examiner* — Aaron Roane

(57) ABSTRACT

A cryoprobe clamp for creating a lesion in a target tissue comprises a housing portion, a handle extending from the housing portion, a clamp assembly including a distal blade and a proximal blade structured for clamping a target tissue therebetween, a trigger mechanism positioned adjacent the handle and operably coupled to the clamp assembly, and an ablation tool extending between the housing portion and the clamp assembly. The distal blade includes receiving means structured to receive a distal portion of the ablation tool, and the proximal blade includes an outer frame surrounding an open window portion. Upon clamping the target tissue between the distal and proximal blades, a lesion formed by the distal end of the ablation tool is visible through the window portion of the proximal blade.

13 Claims, 18 Drawing Sheets

(56) References Cited

U.S. PATENT DOCUMENTS

| | | |
|---|---|---|
| 2005/0113821 A1 | 5/2005 | Pendekanti et al. |
| 2007/0175955 A1 | 8/2007 | Shelton, IV et al. |
| 2008/0045935 A1* | 2/2008 | Cox et al. .................. 606/21 |

* cited by examiner

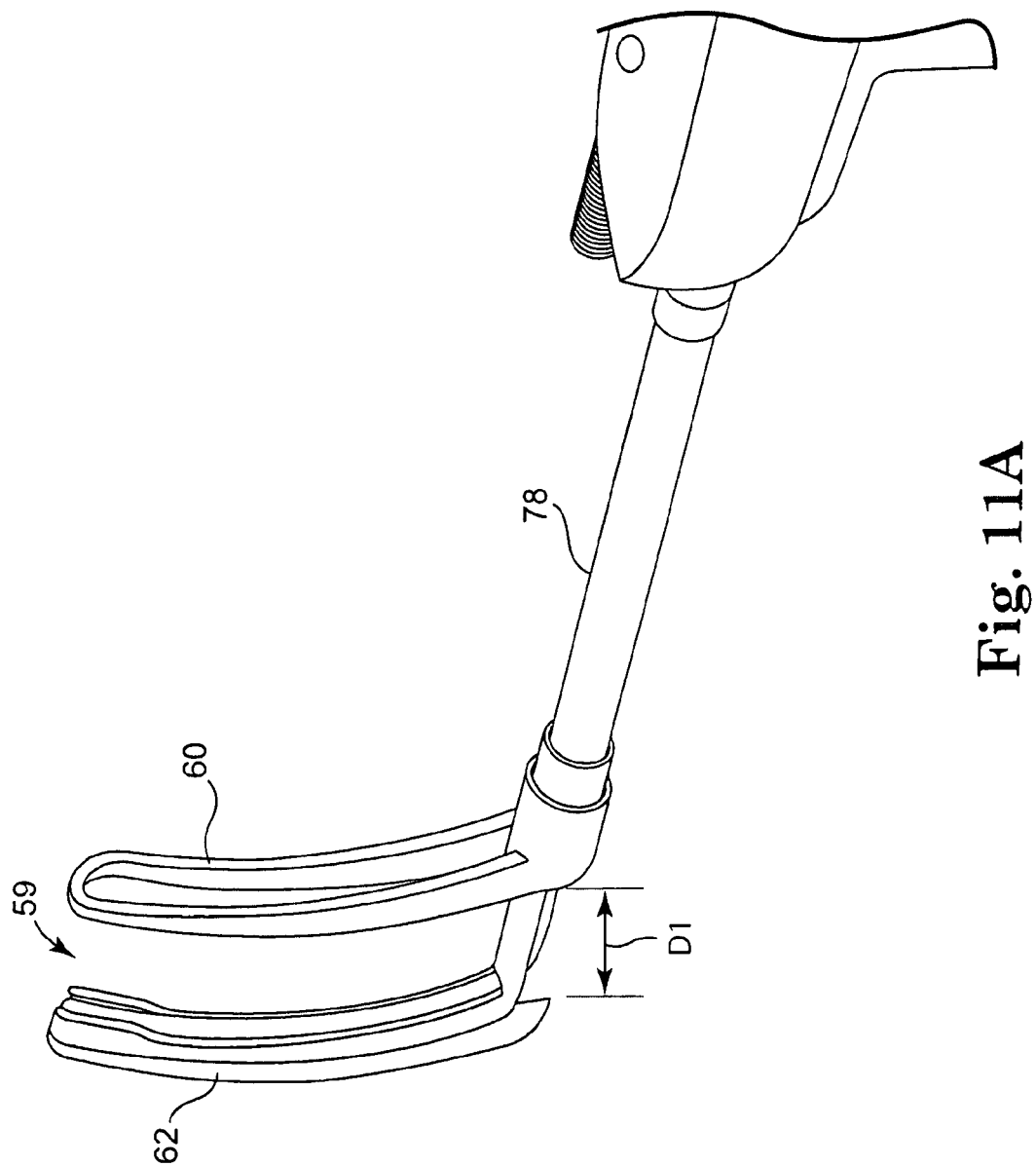

CRYOPROBE CLAMP HAVING TRANSMURALITY ASSESSMENT WINDOW

FIELD OF THE INVENTION

The present invention relates to a method and system for ablating tissue. More particularly the present invention relates to a medical device having a pair of opposing blades, one blade having a window to assess transmurality.

BACKGROUND OF THE INVENTION

It is well documented that atrial fibrillation (AF), either alone or as a consequence of other cardiac disease, continues to persist as the most common type of cardiac arrhythmia. In the United States, AF currently affects an estimated two million people, with approximately 160,000 new cases being diagnosed each year. The cost of treatment for AF alone is estimated to be in excess of $400 million worldwide each year.

AF may be treated using several approaches. Pharmacological treatment is initially the preferred approach, first to maintain normal sinus rhythm. Certain antiarrhythmic drugs, like quinidine and procainamide, can reduce both the incidence and the duration of AF episodes but typically fail to maintain sinus rhythm in the patient. Cardioactive drugs, like digitalis, Beta blockers, and calcium channel blockers, are used to control AF by restoring the heart's natural rhythm and limiting the natural clotting mechanism of the blood. However, antiarrhythmic drug therapy often becomes less effective over time. In addition, antiarrhythmic drugs can have severe side effects, including pulmonary fibrosis and impaired liver function.

A surgical approach known as the "MAZE" procedure was developed, which effectively creates an electrical maze in the atrium and precludes the ability of the atria to fibrillate. Utilizing the MAZE procedure, a surgeon makes strategically placed incisions through the wall of the atrium with a scalpel and then sews the cuts back together, creating a scar pattern. The scars interrupt the conduction routes of the most common reentrant circuits and direct the sinus impulses from the sinoatrial node to the atrioventricular node along a specified route. However, while effective to ablate medically refractory atrial fibrillation, the MAZE procedure is expensive and complicated to perform. Moreover, because the MAZE procedure must be performed as an open-chest procedure, it significantly increases the risk of complication and trauma to the patient.

Minimally invasive techniques were next developed to minimize the long hospital stays associated with open-chest procedures. Typically, these devices have an elongate, highly-flexible shaft with a steerable distal end for negotiating a path through the body of a patient. Rigid shaft devices are used in more invasive procedures where a more local opening or direct access to a treatment site is available or created.

The foregoing devices are intended to ablate through the full thickness of the cardiac wall, and thus create a risk associated with damaging structures within or on the outer surface of the cardiac wall. To address these problems ablation devices were developed which include opposing blade members that ablate tissue from both sides of the cardiac wall. For example, U.S. Pat. No. 5,443,463 to Stern et al., U.S. Pat. No. 5,733,280 to Avitall; U.S. Pat. No. 6,161,543 to Cox et al.; and U.S. Pat. No. 6,517,536 to Hooven et al. all describe techniques for ablating tissue of organs or vessels having opposing walls and also disclose ablation devices having clamping members with opposing jaws that clamp a treatment site therebetween.

Particularly, Stern et al. disclose a method and apparatus for selectively coagulating blood vessels or tissue containing blood vessels that involves the placement of the blood vessels or tissue between the prongs of a forceps with the jaws of the forceps containing a plurality of electrodes which are energized by radio-frequency power. A plurality of sensors are associated with the electrodes and are in contact with the vessels or tissue in order to measure the temperature rise of the tissue or blood vessels and to provide feedback to the radio-frequency power in order to control the heating and perform coagulation of the vessels or tissue.

Avitall discloses probe devices suitable for epicardial mapping and ablation. In one embodiment, the probes are designed to be used directly in an open chest mode during cardiac surgery for the rapid creation of linear lesions on an exposed heart. In another embodiment, the probes are designed to capture myocardial tissue between parallel probe members to create lesions through the tissue thickness. A first probe member may be used to penetrate the myocardial tissue to the inside of an atrial chamber. The first probe member may cooperate with a second probe member disposed on the outer surface.

Cox et el. disclose a system for transmurally ablating heart tissue that includes an ablating probe having an elongated shaft positionable through the chest wall and into a transmural penetration extending through a muscular wall of the heart and into a chamber thereof. The shaft includes an elongated ablating surface for ablating heart tissue. Furthermore, the system includes a sealing device fixable to the heart tissue around the transmural penetration for forming a hemostatic seal around the probe to inhibit blood loss therethrough.

Finally, Hooven et al. disclose a method and apparatus for transmural ablation using an instrument containing two electrodes or cryogenic probes. A clamping force is exerted on the two electrodes or probes such that tissue is clamped therebetween. Bipolar RF energy is then applied between the two electrodes, or the probes are cryogenically cooled, thus ablating the tissue therebetween. As illustrated in FIG. 9 of Hooven et al., the electrodes or cryogenic probes are provided on the center portion of solid jaw members. Consequently, the surgeon cannot visualize the tissue that is clamped between these jaw members during treatment. Therefore, a monitoring device is provided that measures a suitable parameter, such as impedance or temperature, and indicates when the tissue between the electrodes has been fully ablated.

Based on the foregoing, it is apparent that the systems disclosed in Stern et al., Avitall, Cox et al., and Hooven et al. do not allow the surgeon to assess transmurality of a lesion without relying on, for example, temperature or impedance, or without having to first remove the device from the tissue site.

One common element of the devices disclosed in Stern et al., Avitall, Cox et al., and Hooven et al. is that they include rigid members/shafts to facilitate reaching the tissue treatment site. Although a rigid shaft can be provided with a predetermined shape, one must select a device with a rigid shaft that has the most appropriate shape for positioning the working portion of the device in contact with the treatment site in view of the particular anatomical pathway to be followed in the patient. It will be appreciated that a large inventory of devices having rigid shafts may be required to accommodate the various treatment sites and patient anatomies. For example, Cox el al. describe a variety of rigid probe shapes. Further, for a patient having a relatively uncommon anatomic configuration and/or a difficult to reach treatment site, all rigid devices of an existing set may have less than optimal shapes for positioning. This may impair the prospects of successfully carrying out the treatment procedure. For an ablation device which must bear against tissue at the remote region to create lesions, the contour followed by the device in reaching the target site will in general further restrict the direction and magnitude of the movement and forces which may be applied or exerted on the working portion of the device to effect tissue contact and treatment.

U.S. Publication No. 2004/0254606 to Wittenberger et al. discloses a shaft assembly that has malleability such that the shaft assembly retains a first shape until manipulated to a second shape thus purportedly overcoming the problems associated with the foregoing inventions. When positioned, the Wittenberger et al. device includes sensor mechanisms that measure temperature and impedance that are designed to help the surgeon assess transmurality. The resulting temperature or impedance readings provide an indication to the surgeon of the transmurality of the lesion. However, these electrode systems may be prone to breaking down while in use and require an interpolation of transmurality. For example, Wittenberger et al. disclose that transmurality may be ascertained when the temperature sensor detects a temperature of −40 degrees Centigrade for two minutes but that time and temperature may be different for different types, conditions and thicknesses of tissue. Therefore, the surgeon has to remove the clamp from the tissue to visualize whether or not transmurality of the lesion has been achieved. If not the clamp must then be positioned on the tissue again which may result in improper placement with additional tissue being subjected to the procedure, which tissue might not be fully ablated.

Therefore, a need exists for a surgical ablation device that includes a mechanism on the jaws that allows the surgeon to assess transmurality of the lesion without relying on temperature or impedance and without having to remove the clamp from the tissue site.

BRIEF SUMMARY OF THE INVENTION

The present invention advantageously provides a surgical clamp having a pair of opposing blade members that are movable relative to one another from a first position, wherein the blade members are disposed in a spaced apart relation relative to one another, to a second position, wherein the blade members cooperate to grasp tissue therebetween. A flexible ablation tool is connected to at least one of the blade members, such that the blade members are capable of conducting ablation energy through the tissue grasped therebetween.

In yet another exemplary embodiment, a medical device for ablating tissue is provided having a proximal blade and a distal blade, the distal blade including a flexible ablation tool configured to circulate cryogenic fluid therethrough and having at least one ablation segment. The proximal blade includes a window that in operation allows the surgeon to assess transmurality of the lesion. The medical device further includes a handle assembly operably connected to the proximal and distal blades to move the blades from a first position to a second position. An ablation control system is operably connected to the ablation tool.

In an exemplary method, a method of ablating tissue includes the steps of: providing an ablating device having first and second opposing blades positionable from a first position to a second position, wherein the first of said opposing blades includes a flexible ablation tool situated in a holding channel therewithin and the second opposing blade includes a window longitudinally disposed along a length of the second opposing blade; positioning the opposing blades in the first position such that the opposing blades are in a spaced apart relation; placing the opposing blades about the tissue to be treated; positioning the opposing blades in the second position such that the opposing blades grasp the tissue to be treated; ablating the tissue to be treated; and visualizing transmurality without removing the opposing blades from the tissue to be treated.

In another exemplary method, a method for evaluating transmurality of a lesion is provided and includes the steps of positioning a pair of opposing blades about tissue to be treated; applying a cooling element to at least one of the blades; clamping the opposing blades to contact tissue to be treated; measuring temperature from a temperature sensor associated with one of the blades of the ablating device; and visualizing transmurality of the lesion without unclamping the opposing blades.

In another exemplary embodiment, a medical device having ablation and transmurality assessment capabilities is provided having a surgical clamp with transmurality capability, and a flexible ablation tool removably insertable within the surgical clamp.

BRIEF DESCRIPTION OF THE DRAWINGS

FIG. 11A is a perspective view of a fully assembled cryoprobe clamp illustrating opposing blades in the open position.

DETAILED DESCRIPTION OF THE INVENTION

The present invention provides a medical device having a handle assembly for actuating a pair of opposing blade members. The blade members are movable relative to one another from a first position, wherein the blade members are disposed in a spaced apart relation relative to one another, to a second position, wherein the blade members cooperate to grasp tissue therebetween. A flexible ablation tool is connected to at least one of the blade members, such that the blade members are capable of conducting ablation energy through the tissue grasped therebetween.

Figure 1:
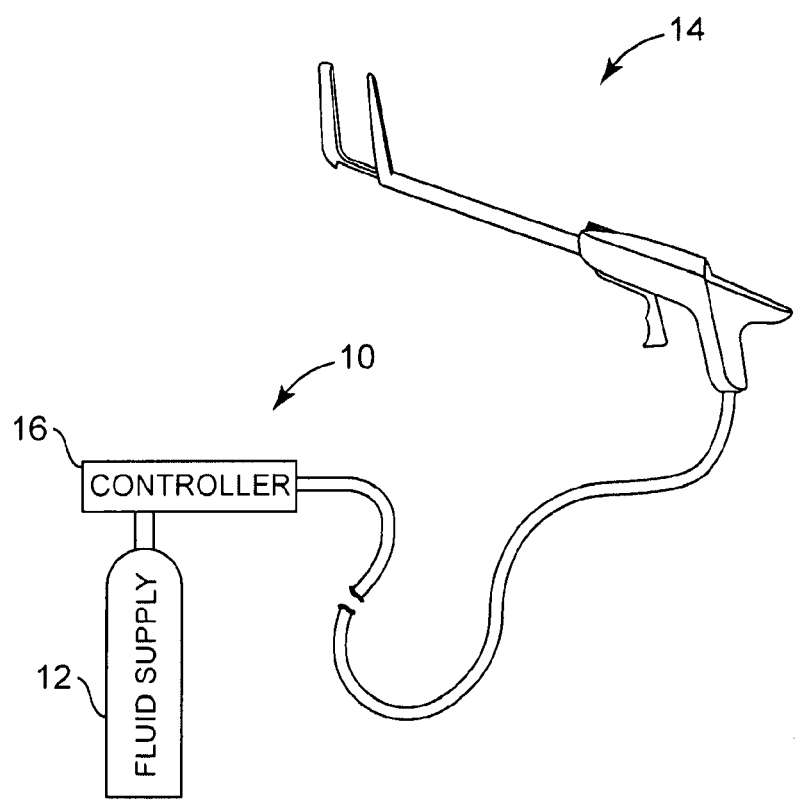
FIG. 1 illustrates an exemplary ablation control system used with the surgical clamp in accordance with the present invention.

FIG. 1 illustrates an exemplary embodiment of an ablation control system 10 in accordance with the present invention. Ablation control system 10 generally includes a supply of cryogenic or cooling fluid 12 in communication with a cryoprobe clamp 14. A fluid controller 16 is interposed or is in-line between the cryogenic fluid supply 12 and the cryoprobe clamp 14 for regulating the flow of cryogenic fluid into the cryoprobe clamp 14 in response to a controller command. Controller 16 commands may include programmed instructions, sensor signals, and manual user input. For example, the fluid controller 16 may be programmed or configured to increase and decrease the pressure of the fluid by predetermined pressure increments over predetermined time intervals.

In another exemplary embodiment, the fluid controller 16 may be responsive to input from a user input device to permit flow of the cryogenic fluid 12 into the cryoprobe clamp 14. In addition, one or more temperature elements in electrical communication with the fluid controller 16 may be provided to regulate or terminate the flow of cryogenic fluid 12 into the cryoprobe clamp 14 when a predetermined temperature at a selected point or points on or within an ablation segment of the cryoprobe clamp 12 is/are obtained. For example, a plurality of temperature elements may be positioned at spaced intervals along an ablation tool coupled to one of the blade members of the cryoprobe clamp 14.

In another exemplary embodiment, one or more sensor mechanisms, such as a ECG leads, in electrical communication with the controller may be provided to regulate or terminate the flow of cryogenic fluid 16 into the ablation tool of the cryoprobe clamp 14 depending on the electrical activity in the tissue being treated. For example, the proximal and distal blades (which will be discussed in more detail to follow) of the cryoprobe clamp 14 may provide feedback that permits a user to gauge the completeness of the ablation. Specifically, a lesion blocks electrical signals because it is non-conductive scar tissue. The proximal and distal elongated blades may be used to measure the ability of the lesion to block an electrical signal. For example, an electrode may be affixed one each to the distal ends of the proximal and distal blades and used to verify electrical isolation of the lesion created by the ablation tool in the cryoprobe clamp 14. An electrical signal may be transmitted from one electrode, through the lesion, to the opposite electrode. The lesion may be considered electrically isolated if the receiving electrode is electrically silent to the signal. Alternatively, the electrical sensor mechanisms may be replaced or supplemented with pressure sensors. The pressure sensors may be used to determine when the ablation segment is in physical contact with the tissue to be treated.

The cryogenic fluid may be in a liquid or a gas state, or a combination thereof. An extremely low temperature may be achieved within the cryoprobe clamp 14, and more particularly at the ablation segment, by cooling the fluid to a predetermined temperature prior to its introduction into the cryoprobe clamp, by allowing a liquid state cryogenic fluid to boil or vaporize, or by allowing a gas state cryogenic fluid to expand. Exemplary liquids include chlorodifluoromethane, polydimethylsiloxane, ethyl alcohol, HFC's such as AZ-20 (a 50-50 mixture of difluoromethane & pentafluoroethane sold by Allied Signal), and CFC's such as DuPont's Freon. Exemplary gasses include argon, nitrous oxide, and carbon dioxide.

Figure 2:
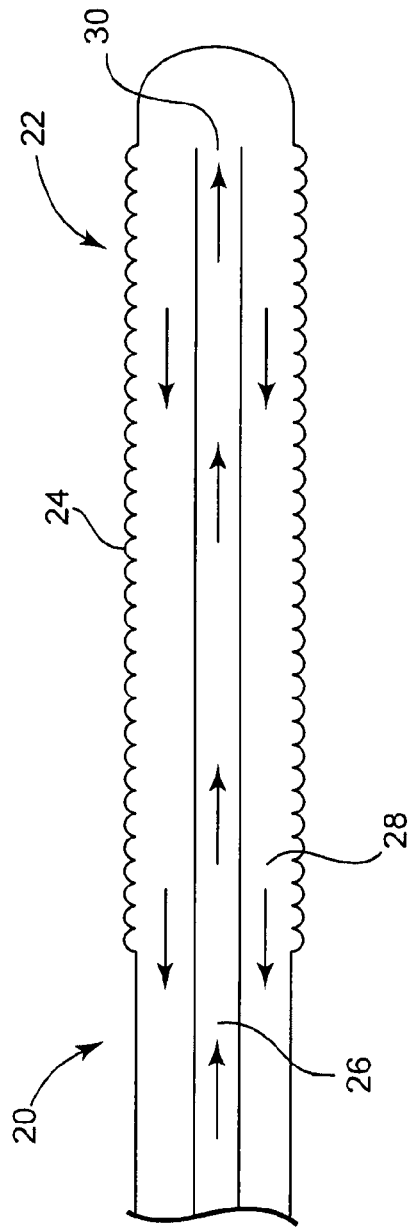
FIG. 2 is a cross-sectional view of one ablation tool in accordance with the present invention.

FIG. 2 illustrates one embodiment of an ablation tool 20 that may be used in conjunction with the cryoprobe clamp in accordance with the present invention. Referring to FIG. 2, the ablation tool 20 includes an ablation segment 22 having a thermally-transmissive region 24, and defining a fluid path having at least one fluid inlet 26 and at least out fluid outlet 28 to the ablation segment 22, wherein the fluid inlet 26 is in fluid communication with a cryogenic fluid source. An orifice 30 at the distal end of the fluid inlet 26 is structured to distribute fluid from the fluid inlet 26 to the fluid outlet 28.

Even though many materials and structures may be thermally conductive or thermally transmissive if chilled to a very low temperature and/or cold soaked, as used herein, a "thermally-transmissive region" is intended to broadly encompass any structure or region of the ablation tool 20 that readily conducts heat. For example, a metal structure exposed (directly or indirectly) to the cryogenic fluid path is considered a thermally-transmissive region even if an adjacent polymeric or latex portion also permits heat transfer, but to a much lesser extent than the metal. Thus, the thermally-transmissive region 24 may be viewed as a relative term to compare the heat transfer characteristics of different regions or structures, regardless of the material.

As illustrated in FIG. 2, the thermally-transmissive region 24 may have a generally bellows-shaped configuration. In one alternative embodiment, the thermally-transmissive region 24 may include, for example, a single, continuous, and uninterrupted surface or structure. In yet another alternative embodiment, the thermally-transmissive region 24 may include multiple, discrete, thermally-transmissive structures that collectively define a thermally-transmissive region that is elongate or linear.

Depending on the ability of the cryogenic system, or portions thereof, to handle given thermal loads, the ablation of an elongate tissue path may be performed in a single or multiple cycle process with or without having to relocate the ablation tool 20 one or more times across tissue.

Figure 3:
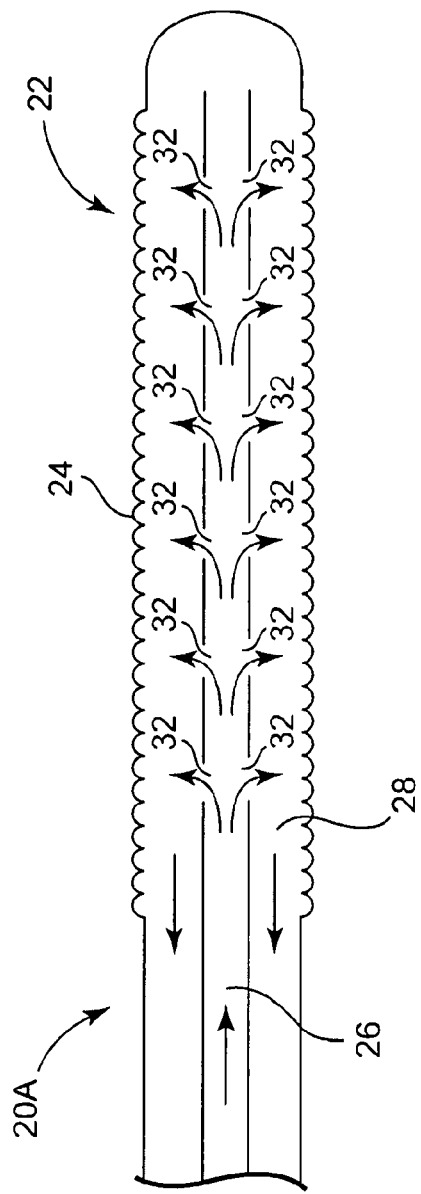
FIG. 3 is a cross-sectional view of a second ablation tool in accordance with the present invention.

FIG. 3 illustrates a second exemplary embodiment of an ablation tool. In particular, ablation tool 20A is similar to ablation tool 20 previously described above in reference to FIG. 2. However, instead of having a single orifice 30 at the distal end of the fluid inlet 26, the ablation segment of ablation tool 20A includes a plurality of spaced apart orifices 32 structured to direct the fluid between the fluid inlet 26 and the fluid outlet 28.

Figure 4:
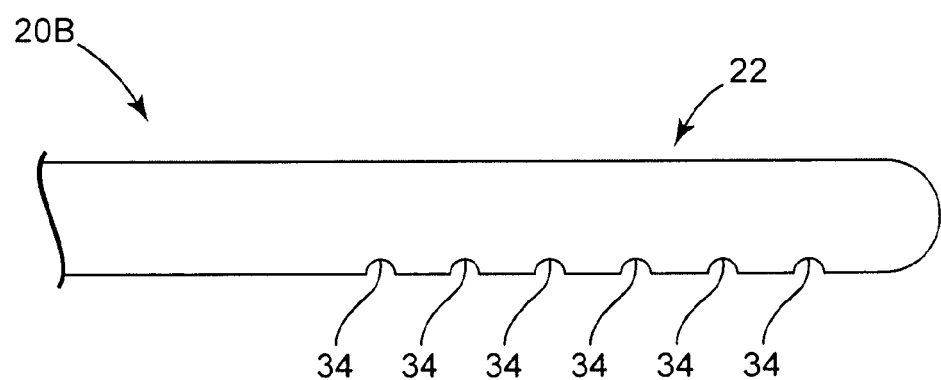
FIG. 4 is a sectional view of a segment of a third ablation tool in accordance with the present invention.

FIG. 4 illustrates a third exemplary embodiment of an ablation tool. As shown in FIG. 4, ablation tool 20B includes an ablation segment 22 having a plurality of orifices 34 that enable the application of cryogenic fluid directly onto the tissue to be treated.

The ablation tools described above in reference to FIGS. 2-4 are merely three embodiments of ablation tools that may be used in conjunction with the cryoprobe clamp in accordance with the present invention, and are presented herein for purposes of example and not limitation. Thus, workers skilled in the art will appreciate that numerous other types of ablation tools may be adapted for use with the cryoprobe clamp without departing from the intended scope of the present invention.

Figure 5:
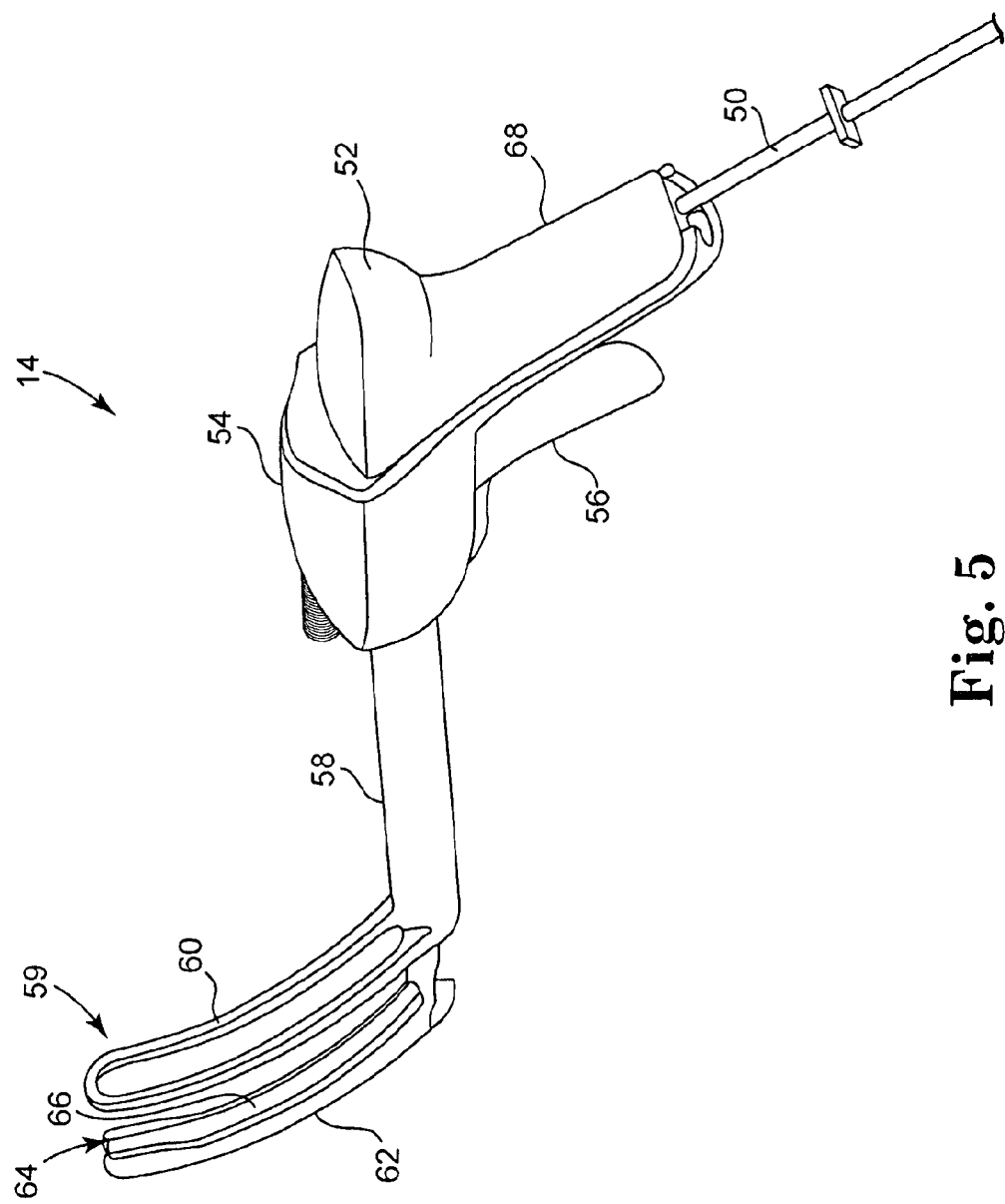
FIG. 5 is a perspective view of the cryoprobe clamp in accordance with the present invention.
Figure 6:
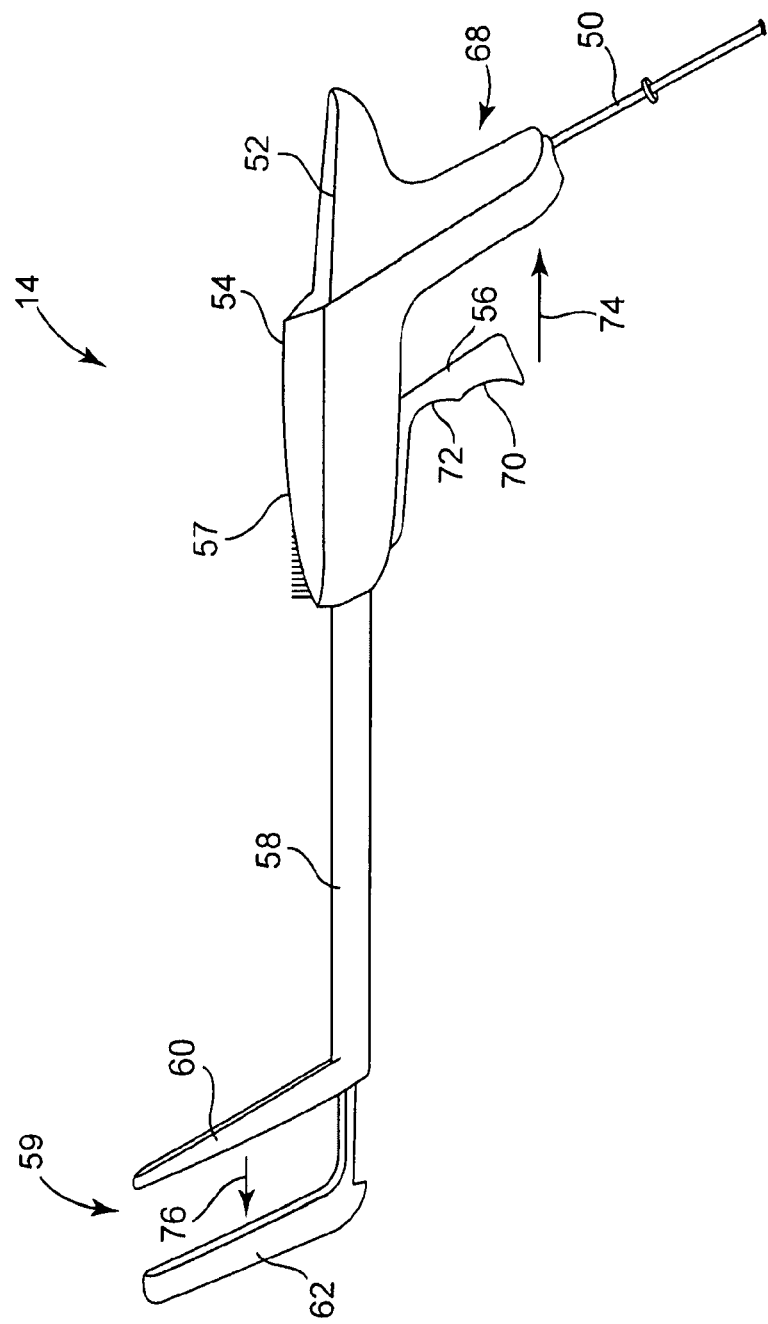
FIG. 6 is a side view of the cryoprobe clamp in accordance with the present invention.

FIGS. 5 and 6 are perspective and side views, respectively, of the cryoprobe clamp 14 in accordance with the present invention. Cryoprobe clamp 14 may generally include cryogenic fluid line 50, proximal housing 52, distal housing 54, trigger member 56, offset slider 57, outer tube 58, clamp assembly 59 having proximal blade 60 and distal blade 62, and ablation tool 64 having thermally transmissive region 66.

Outer tube 58 may be coupled on a proximal end to offset slider 57 and on a distal end to proximal blade 60. Furthermore, outer tube 58 may be hollow and structured to slide in a longitudinal direction on an inner tube coupled to distal blade 62. As will be discussed in detail to follow, actuating trigger member 56 results in translational movement of offset slider 57, which is therefore transferred to proximal blade 60 through outer tube 58.

Ablation tool 64 may be similar to one of ablation tools 20, 20A, or 20B described above. However, as stated previously, numerous other embodiments of ablation tools may be used without departing from the intended scope of the invention.

As shown in FIGS. 5 and 6, a bottom portion of proximal housing 52 and distal housing 54 form a handle 68. Upon grasping handle 68, a surgeon preferably places his middle finger of the same hand on a lower portion 70 of trigger member 56, and his index finger on an upper portion 72 of trigger member 56. The surgeon is then able to comfortably pull trigger member 56 in the proximal direction indicated by arrow 74 to initiate translational movement of offset slider 57 and proximal blade 60 toward distal blade 62 in the distal direction indicated by arrow 76 in order to grasp tissue between the blades.

FIGS. 7-10 illustrate perspective views of clamp assembly 59 in various assembled and unassembled states. Outer tube 58 has also been removed such that inner tube 78 is visible. Inner tube 78 may provide a pathway for ablation tool 64 between distal blade 62 and distal housing 54. Proximal blade 60 may include an outer frame 79 that surrounds and defines an open window portion 80 structured to enable the surgeon to view the tissue that is clamped between proximal blade 60 and distal blade 62 during a cryosurgery procedure. The distal side of outer frame 79 may include a tissue engaging surface 81 that is structured to engage and apply pressure to a target tissue clamped between proximal blade 60 and distal blade 62.

Figure 7:
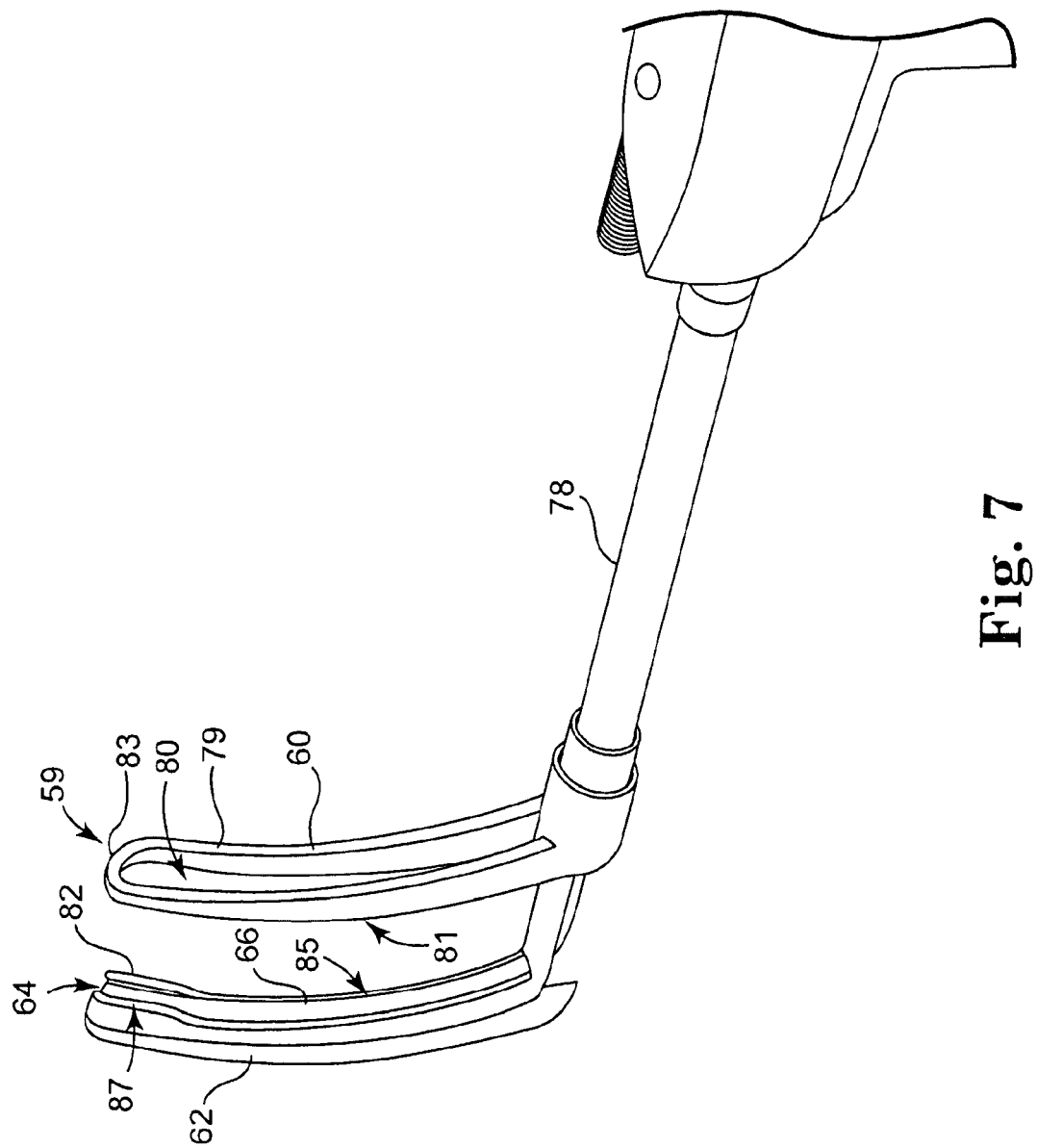
FIG. 7 is a perspective view showing detail of the opposing blades including window.
Figure 8:
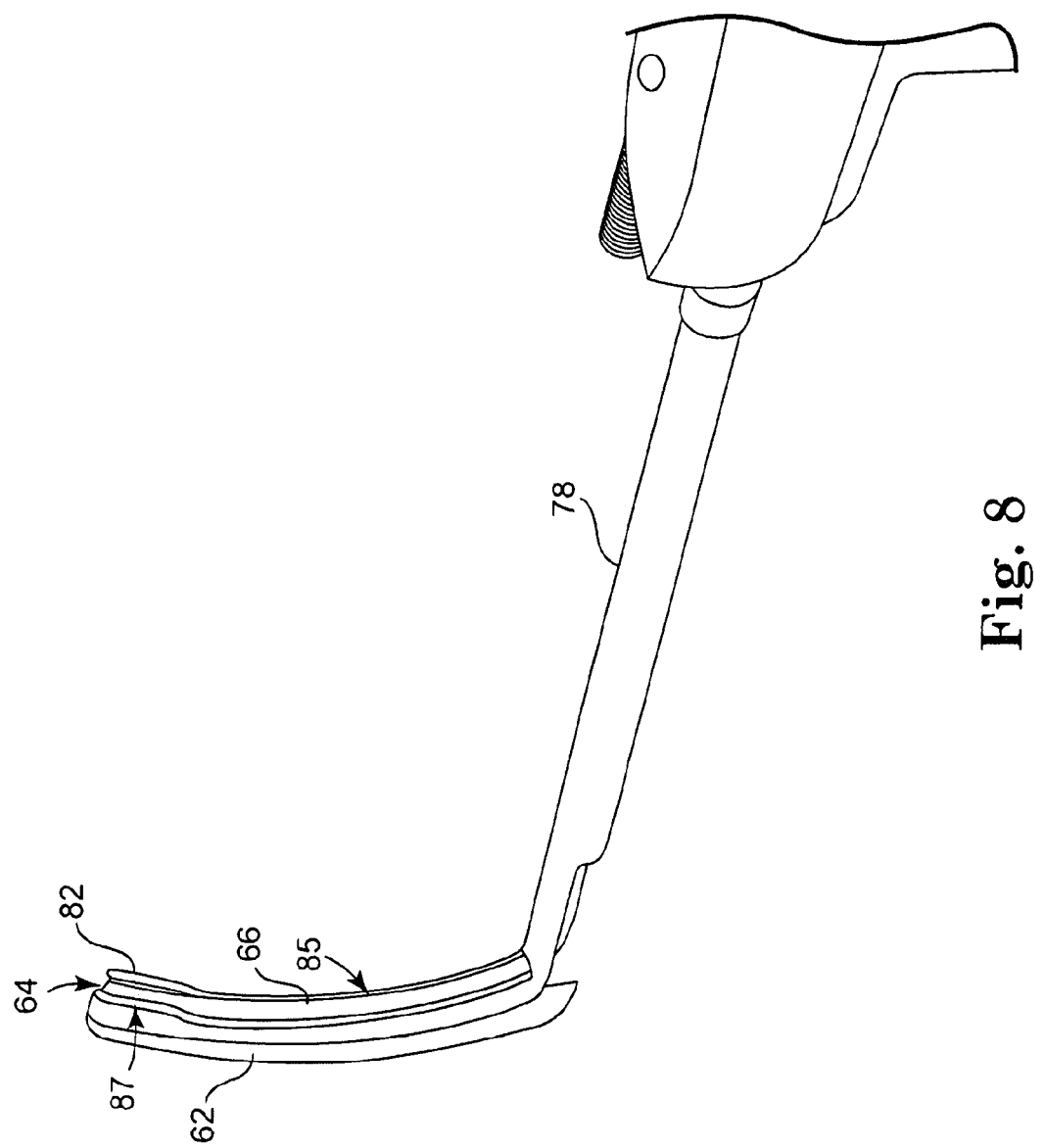
FIG. 8 is a perspective view of the distal blade of the cryoprobe clamp in accordance with the present invention.
Figure 9:
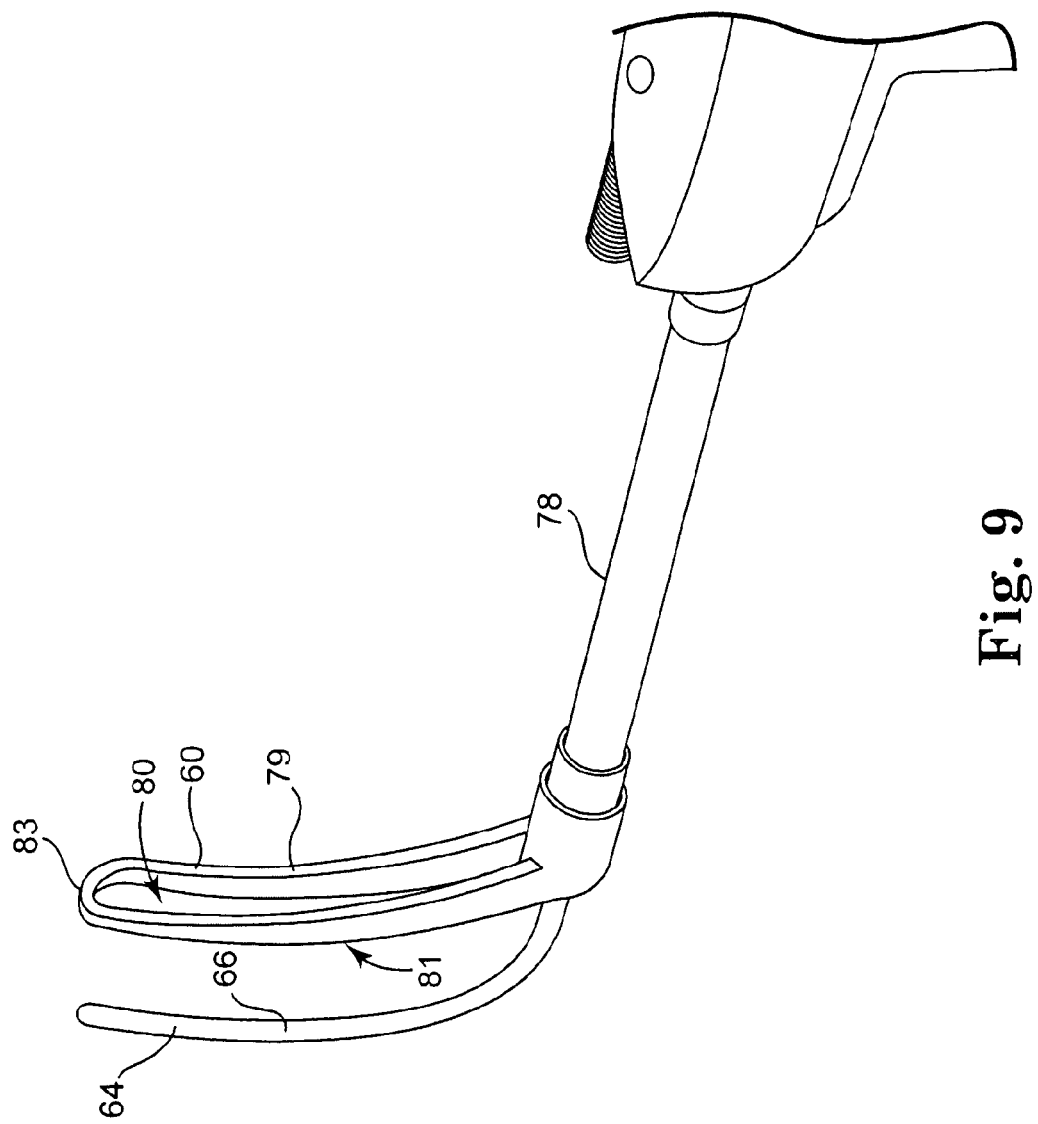
FIG. 9 is a perspective view of the proximal blade with window including flexible ablation tool.
Figure 10:
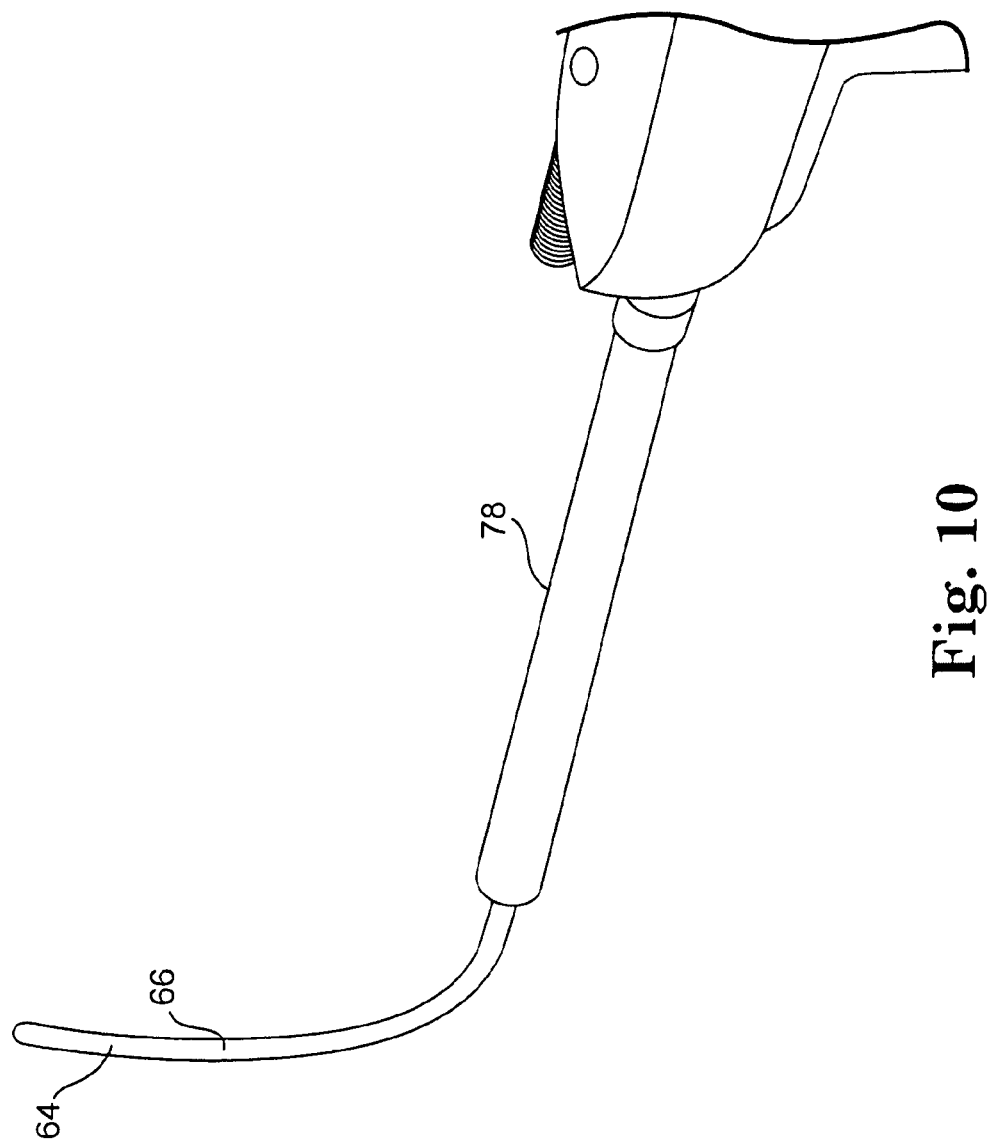
FIG. 10 is a perspective partial view of the cryoprobe clamp in accordance with the present invention showing flexible ablation tool.

As illustrated in FIG. 7, window portion 80 of proximal blade 60 is surrounded on all sides by outer frame 79. Furthermore, window portion 80 is disposed along substantially the entire length of proximal blade 60. However, those skilled in the art will appreciate that numerous other window configurations, window shapes, and window sizes may be utilized without departing from the intended scope of the present invention. For example, in one alternative embodiment of proximal blade 60, a top portion 83 of outer frame 79 may be removed such that outer frame 79 is generally "U-shaped." In another alternative embodiment, proximal blade 60 is substantially as shown in FIG. 7, but further includes a transparent cover over window portion 80. The transparent cover may be formed from any suitable material, including but not limited to glass or plastic. In yet another alternative embodiment, the transparent cover may be a magnifying lens structured to provide the surgeon with a close-up, more detailed view of the lesion formed by thermally transmissive region 66 of ablation tool 64.

Distal blade 62 may include a distal blade liner 82 coupled to or formed integral with the distal blade and structured to serve as a receiving means for ablation tool 64. As illustrated in FIG. 7, distal blade liner 82 may structured to define a channel 85 along the length of distal blade 62, and may include retaining means 87 for retaining ablation tool 64 within blade liner 82. Retaining means 87 may comprise, for example, a pair of flanges extending over a portion of channel 85. However, numerous other retaining means 87 are contemplated and within the intended scope of the present invention.

As will be appreciated by those skilled in the art, distal blade liner 82 may be structured to serve as a partial sheath that may cover, for example, the back and a portion of the sides of ablation tool 64. One benefit of providing a sheath is that it may limit the effective portion of thermally transmissive region 66 available for creating lesions. This may improve the surgeon's ability to more accurately form a lesion at the intended treatment area.

Clamp assembly 59 is illustrated in FIGS. 7-10 with a "solid" distal blade 62 and a proximal blade 60 with a window portion 80 merely for purposes of example and not limitation. Thus, embodiments of clamp assembly 59 that also include a window portion in distal blade 62 are also possible. However, those skilled in the art will appreciate that because distal blade 62 is positioned behind tissue during treatment and only proximal blade 60 is generally visible, placing a window portion in distal blade 62 may not provide any additional benefits. Furthermore, having a solid distal blade 62 may be advantageous because it may provide increased contact area and increased pressure when tissue is clamped between distal blade 62 and tissue engaging surface 81 of proximal blade 60.

Figure 11B:
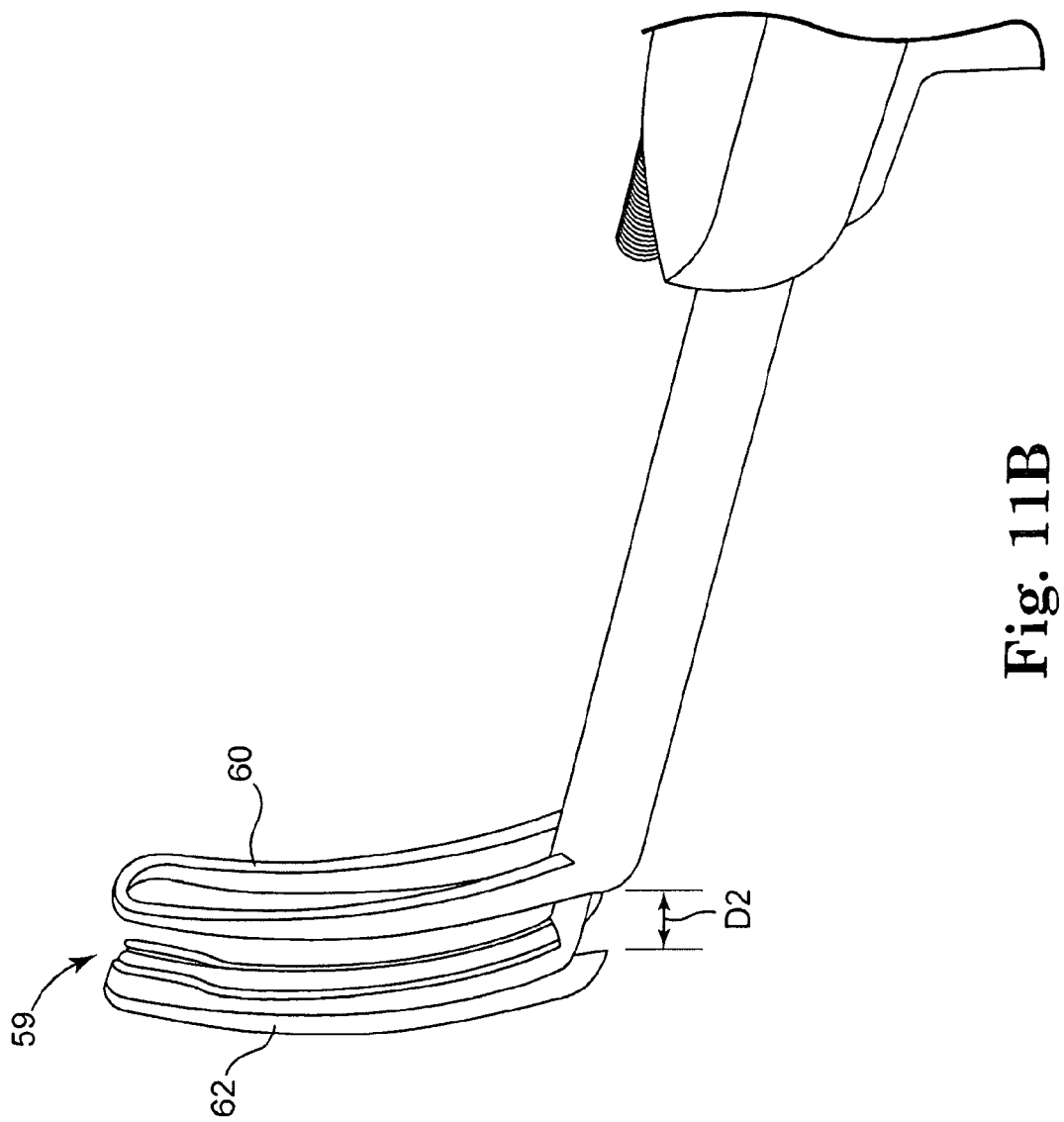
FIG. 11B is a perspective view of the cryoprobe clamp illustrating opposing blades in the clamped position.

FIGS. 11A and 11B illustrate the translational movement of proximal blade 60 with respect to distal blade 62 upon pulling trigger member 56 as previously discussed. In particular, prior to actuating trigger member 56 to initiate the "clamping" between the blades, proximal blade 60 and distal blade 62 are separated by a distance D1. Then, upon actuating trigger member 56, proximal blade 60 is pushed longitudinally toward distal blade 62, and the blades are now separated by a distance D2, which is less than distance D1.

It should be noted, and those skilled in the art will appreciate, that although embodiments of the present invention are described such that proximal blade 60 is pushed longitudinally toward distal blade 62 upon actuating trigger member 56, alternative embodiments may be structured such that distal blade 62 is pulled longitudinally toward proximal blade 60 without departing from the intended scope of the present invention.

Figure 12:
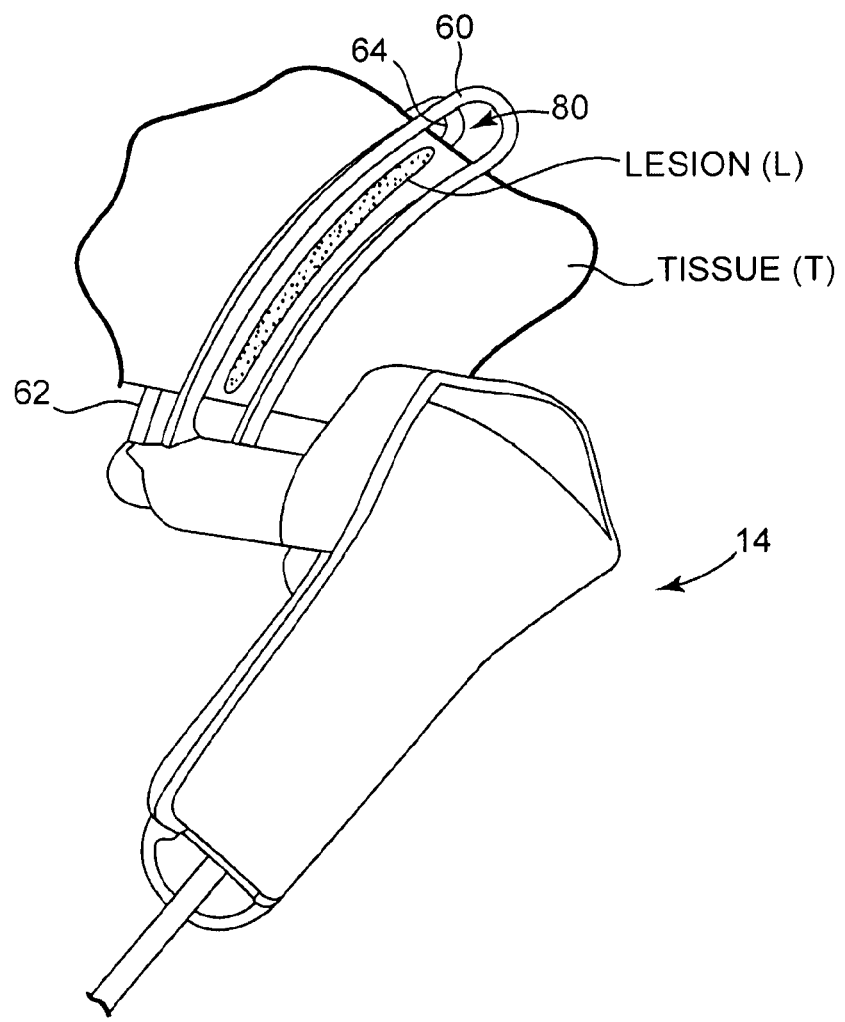
FIG. 12 is a rear perspective view of the cryoprobe of the present invention wherein opposing blades engage treated tissue and transmurality is visualized.

FIG. 12 is a rear perspective view of cryoprobe clamp 14 engaging tissue T for treatment. As will be appreciated by those skilled in the art, when trigger member 56 is actuated to move proximal blade 60 toward distal blade 62, ablation tool 64 is aligned substantially with window portion 80 of proximal blade 60. Consequently, when cryoprobe clamp 14 is operated so that thermally transmissive region 66 of ablation tool 64 creates a lesion L in tissue T, the lesion L may be visible to the surgeon through window 80 in proximal blade 60. Thus, rather than waiting until lesion L is so large that it is visible around the outer dimensions of proximal blade 60, the surgeon is able to verify the formation of lesion L at an earlier time by directly viewing lesion L through window 80 due to the alignment of ablation tool 64 with window 80.

As will be appreciated by those skilled in the art, window portion 80 in proximal blade 60 may allow the surgeon to visually assess transmurality of a lesion without having to remove clamp assembly 59 from the tissue site. As will be further appreciated by those skilled in the art, the ability to perform a visual assessment in accordance with the present invention may be combined with a system having a monitoring device that measures a suitable parameter, such as impedance or temperature, in order to indicate when a lesion has been fully formed. Providing a means for visually assessing the formation of a lesion may allow the surgeon to confirm the feedback from the monitoring device without having to remove the clamp assembly.

Figure 13:
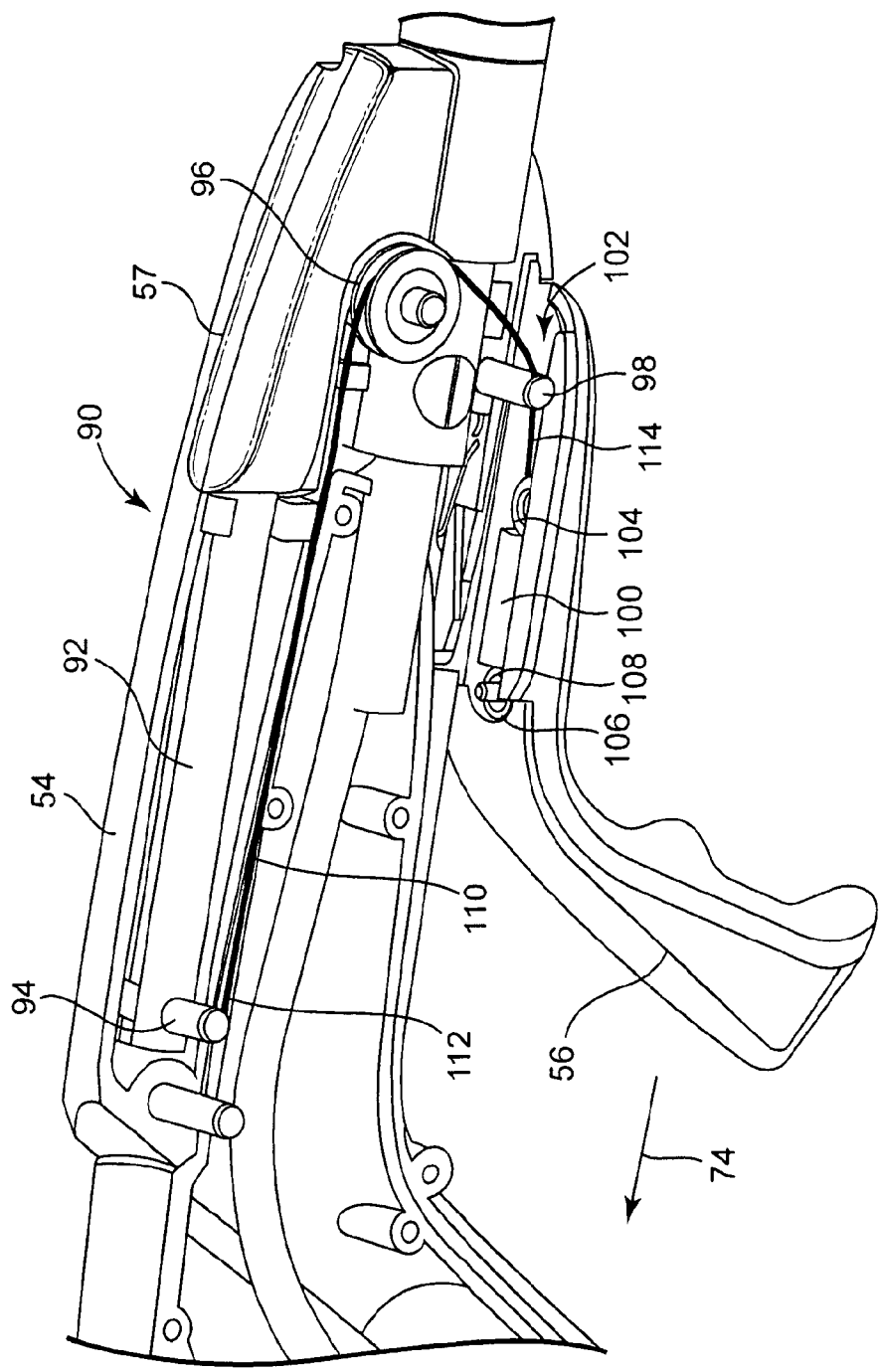
FIG. 13 is a side perspective view of the trigger drive mechanism of the cryoprobe clamp in accordance with the present invention.

FIG. 13 is a view illustrating a trigger drive mechanism 90 within cryoprobe clamp 14. Drive mechanism 90 may generally include spring rod 92, spring rod pin 94, pulley 96, guide pin 98, and extension spring 100. Spring rod 92 may be disposed within distal housing 54, may be coupled on a distal end to offset slider 57, and may be slidable relative to distal housing 54. Pulley 96 and guide pin 98 may be fixed relative to distal housing 54. Finally, extension spring 100 may be disposed within a channel 102 in a top portion of trigger member 56. As illustrated in FIG. 13, extension spring 100 may include first circular hook 104 and second circular hook 106. Second circular hook 106 may be positioned over a spring pin 108 coupled to trigger mechanism 56.

An elongate wire 110 may operably couple the various components of trigger drive mechanism 90 together. Particularly, wire 110 may be coupled on a first end 112 to spring rod pin 94 and on a second end 114 to first circular hook 104 of extension spring 100. As shown in FIG. 13, wire 110 may extend from spring rod pin 94 around pulley 96, then beneath guide pin 98 and to first circular hook 104.

As will be appreciate by those skilled in the art, as trigger mechanism 56 is pulled backward in a proximal direction indicated by arrow 74, second end 114 of wire 110 may also be pulled back in the proximal direction due to the attachment to extension spring 100. Both pulley 96 and guide pin 98 may help to guide wire 110 as second end 114 is being pulled by trigger mechanism 56. At the same time, first end 112 of wire 110 may be pulled in the distal direction, thereby causing spring rod 92 and attached offset slider 57 to also move in the distal direction. This movement of slider 57 causes the "clamping" movement of proximal blade 60 as discussed above in reference to FIGS. 11A and 11B.

Figure 14:
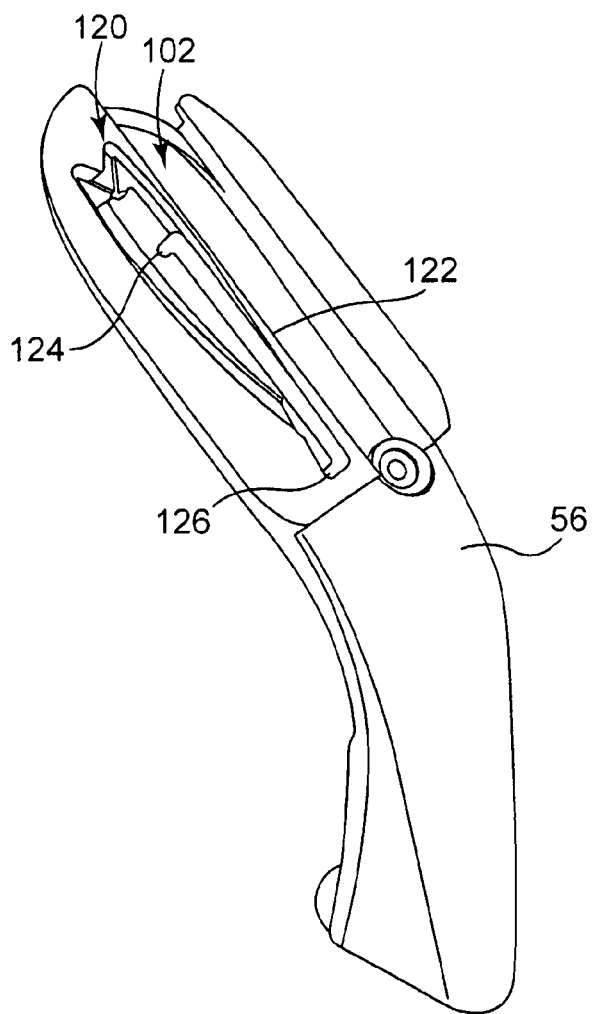
FIG. 14 is a top perspective view of the trigger drive mechanism of the cryoprobe in accordance with the present invention illustrating inlaid track.

FIG. 14 is a top perspective view of trigger mechanism 56 illustrating an inlaid track 120. Track 120 may be designed to create a pathway for bar 122. In particular, bar 122 may be coupled on a distal end 124 to distal housing 54. A proximal end 126 of bar 122 may be structured to "ride" within track 120 as trigger member 56 is actuated. As will be apparent from the following Figures and corresponding discussion, track 120 and bar 122 may function together to create a locking mechanism for trigger member 56.

Figure 15:
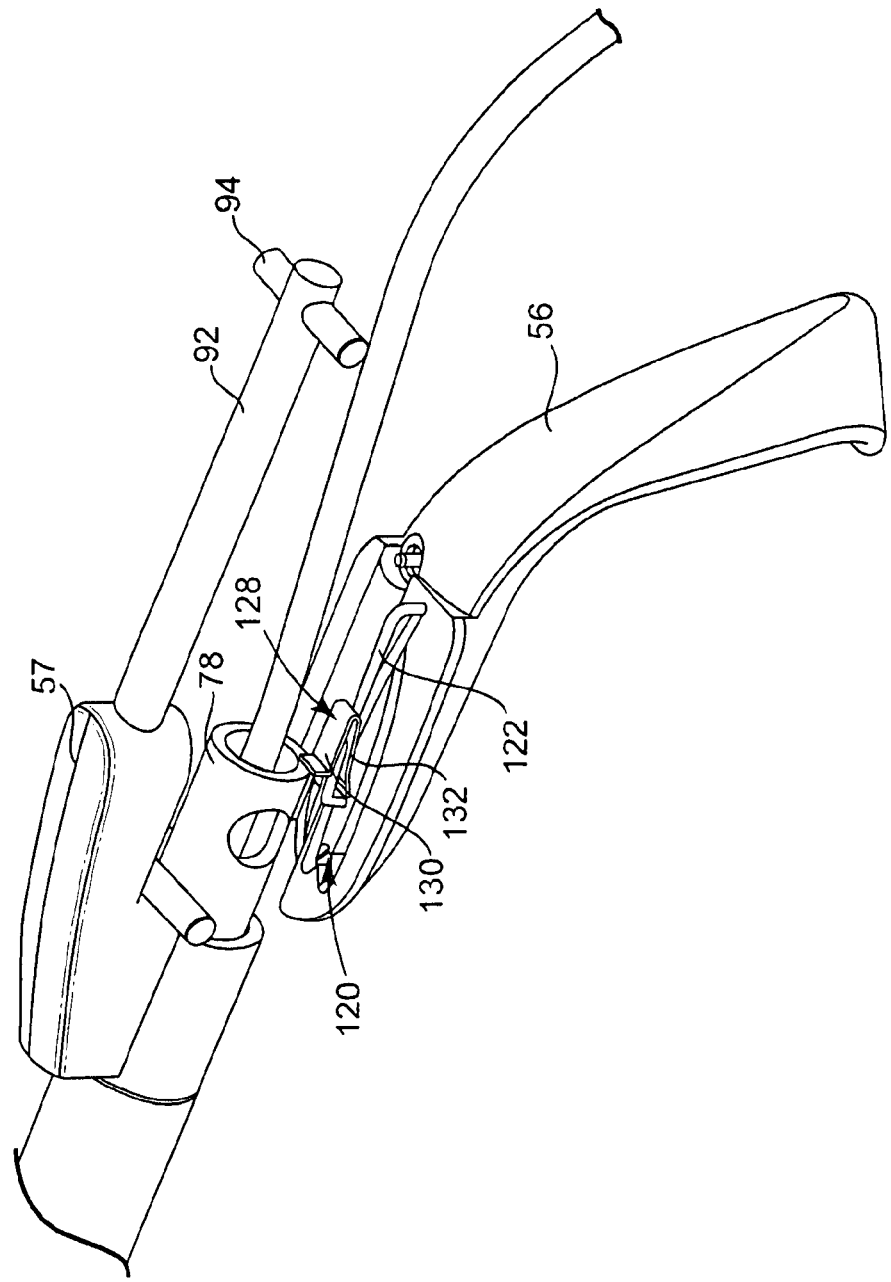
FIG. 15 is a perspective view of the trigger drive mechanism of the cryoprobe in accordance with the present invention opposite that of FIG. 14.

FIG. 15 is a perspective view of cryoprobe clamp 14 on the side opposite that shown in FIG. 14, wherein both proximal and distal housings 52 and 54 have been removed to more clearly see the top portion of trigger member 56. As shown in FIG. 15, a bar spring 128 may be disposed between and engage inner tube 78 and bar 122. In particular, a top portion 130 of bar spring 128 may engage the proximal end of inner tube 78, while a bottom portion 132 of bar spring 128 may engage bar 122. Bar spring 128 may be structured to cause bar 122 to be spring biased toward the center of the top portion of trigger mechanism 56, thus biasing proximal end 126 of bar 122 to remain within track 120.

Figure 16:
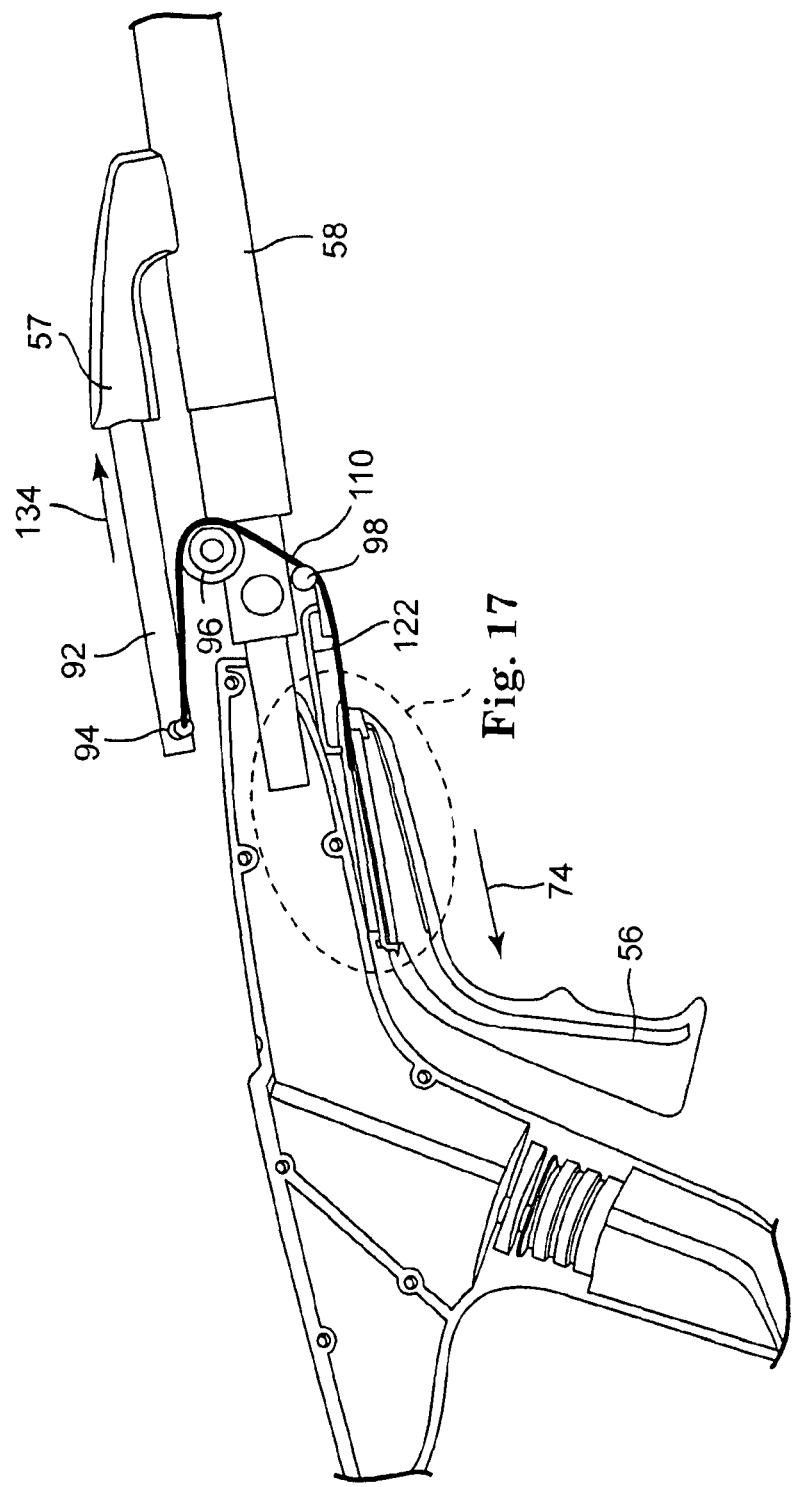
FIG. 16 is a side perspective view of trigger drive mechanism illustrating operation.

FIG. 16 is a view illustrating operation of the trigger drive mechanism 90 within cryoprobe clamp 14. As shown in FIG. 16, when trigger mechanism 56 is pulled backward in the proximal direction indicated by arrow 74, second end 114 of wire 110 may also be pulled back in the proximal direction indicated by arrow 74. As a result, first end 112 of wire 110 may be pulled in the distal direction indicated by arrow 134, thereby causing spring rod 92 and attached offset slider 57 and outer tube 58 to also move in the distal direction. As a result, proximal blade 60 may be moved longitudinally toward distal blade 62 to allow tissue to be clamped between the blades for treatment as previously illustrated in FIG. 12.

As shown in FIG. 16, trigger member 56 is now "locked." This enables the surgeon to remove his fingers from trigger member 56 while proximal and distal blades 60 and 62 remain clamped together with tissue disposed therebetween. When trigger member 56 is locked, proximal end 126 of bar 122 is disposed within a "V-shaped" channel in track 120 positioned between the "lock pathway" for clamping together proximal and distal blades 60 and 62, and the "unlock pathway" for releasing proximal and distal blades 60 and 62 from their clamped position (see FIG. 18 for an illustration of the "pathways"). This V-shaped channel in track 120 defines a "locked position" of proximal end 126 of bar 122 within track 120. As will be appreciated by those skilled in the art, proximal end 126 of bar 122 slides to this locked position within track 120 while trigger member 56 is being pulled in the proximal direction illustrated in FIG. 16.

Figure 17:
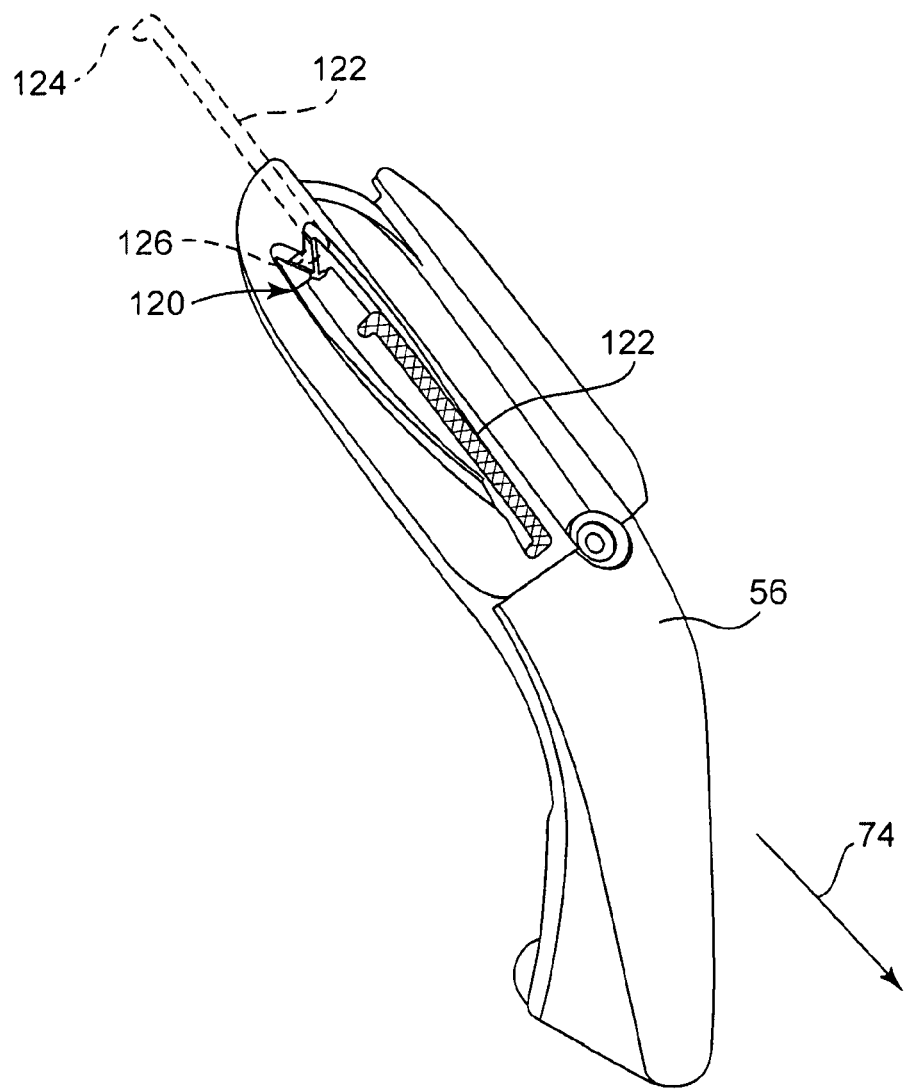
FIG. 17 is a top perspective view of trigger drive mechanism in the locked position.

FIG. 17 is a top perspective view of trigger member 56 illustrating the position of bar 122 (shown in phantom lines) in the "locked" trigger position. As clearly illustrated in FIG. 17, in the locked trigger position, proximal end 126 of bar 122 has slid within track 120 until it engages with the "V-shaped" channel. In this position, trigger member 56 is now locked, and if no further action is taken, proximal blade 60 and distal blade 62 will remain clamped together.

When the surgeon desires to "unlock" the trigger member 56 and clamp assembly 59, he once again pulls trigger member 56 in the proximal direction as indicated by the direction of arrow 74. When trigger member 56 is actuated in such manner, proximal end 126 of bar 122 slides into the "unlock pathway" (see FIG. 18) and returns to the position illustrated by the cross-hatched bar 122 in FIG. 17.

Figure 18:
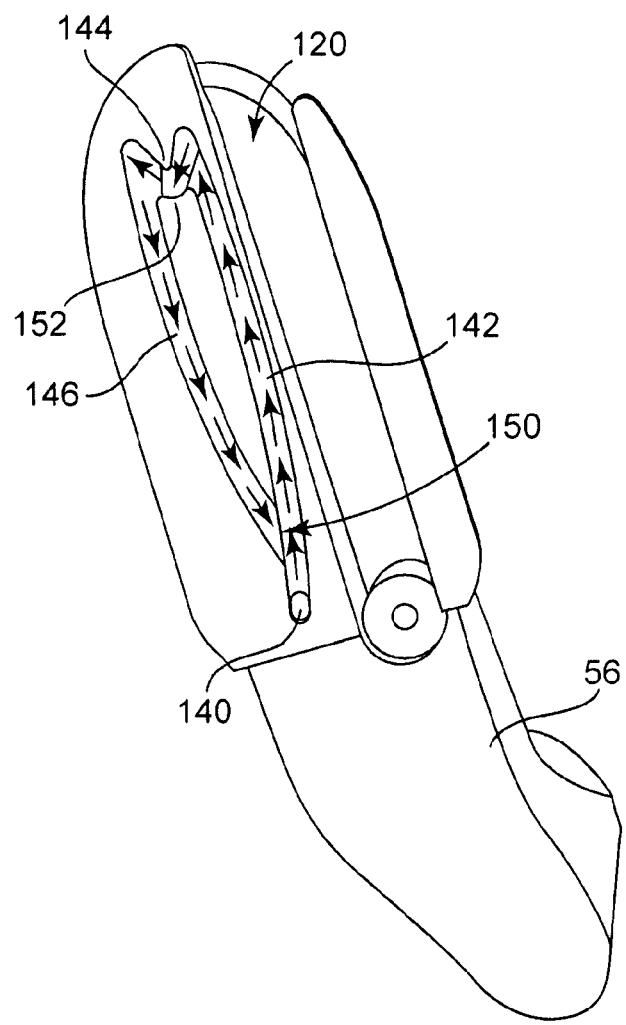
FIG. 18 is a top perspective view of trigger drive mechanism depicting the start position, lock pathway, locked position and unlock pathway.

FIG. 18 is a top perspective view of track 120 of trigger member 56 illustrating the start position 140, lock pathway 142, locked position 144, and unlock pathway 146. As shown in FIG. 18, movement of proximal end 126 of bar 122 within track 120 throughout the entire process of locking and unlocking trigger member 56 and clamp assembly 59 is also represented by a series of arrows.

As illustrated in FIG. 18, there may be an elevation change in the floor of track 120 such that proximal end 126 of bar 122 "drops" down when it approaches these elevation changes. In particular, a first change in elevation may occur near area 150 such that, from start position 140, proximal end 126 of bar 122 must travel down lock pathway 142 and cannot enter unlock pathway 146. A second change in elevation may occur near area 152 such that proximal end 126 of bar 122 drops down into the locked position 144. This prevents proximal end 126 of bar 122 from sliding back to start position 140 via lock pathway 142. Thus, such changes in elevation help to ensure track 120 operates only as a one-way path for proximal end 126 of bar 122.

Although the present invention has been described with reference to preferred embodiments, workers skilled in the art will recognize that changes may be made in form and detail without departing from the spirit and scope of the invention.

What is claimed is:
1. A method of using an ablating device comprising:
providing an ablating device having first and second opposing blades moveable between a first spaced apart position and a second spaced apart position, wherein the first opposing blade includes an ablation tool disposed within a holding channel there within, and wherein the second opposing blade includes a window longitudinally disposed along a length of the second opposing blade;

positioning the first and second opposing blades in the first spaced apart position;

placing the first and second opposing blades about tissue;

positioning the first and second opposing blades in the second spaced apart position such that the first and second opposing blades grasp the tissue;

forming a lesion in the tissue solely by the ablation tool of the first opposing blade; and assessing transmurality of the lesion formed by the ablation tool without removing the first and second opposing blades from the target tissue by visualizing the lesion formed solely by the ablation tool through the window in the second opposing blade.

2. The method of claim 1, wherein the ablation tool is a flexible ablation tool.

3. The method of claim 1, wherein the second opposing blade includes an outer frame surrounding the window.

4. The method of claim 3, wherein the outer frame of the second opposing blade has a tissue engaging surface.

5. The method of claim 1, wherein the ablation device further comprises a trigger mechanism for controlling movement of the first and second opposing blades between the first spaced apart position and the second spaced apart position.

6. The method of claim 5, wherein the step of positioning the first and second opposing blades in the second spaced apart position such that the first and second opposing blades grasp the target tissue to be treated further comprises locking the first and second opposing blades in the second spaced apart position with a locking mechanism.

7. The method of claim 1, wherein the first opposing blade further includes retaining means structured to cover a portion of the holding channel to prevent separation of the ablation tool from the first opposing blade.

8. The method of claim 1, wherein the holding channel of the first opposing blade is positioned such that the ablation tool is aligned with the window of the second opposing blade in the second spaced apart position.

9. The method of claim 1, wherein ablating device does not provide an ablation tool with the second opposing blade.

10. The method of claim 1, wherein the second opposing blade defines a thickness, and further wherein the window is defined by the absence of material through an entirety of the thickness of the second opposing blade.

11. The method of claim 1, wherein the step of positioning the first and second opposing blades in the second spaced apart position includes transitioning the opposing blades from the first spaced apart position to the second spaced apart position, the step of transitioning including the ablation tool moving relative to the window.

12. A method of using an ablating device comprising:

providing an ablating device having first and second opposing blades moveable between a first spaced apart position and a second spaced apart position, wherein the first opposing blade includes an ablation tool disposed within a holding channel there within, and wherein the second opposing blade includes a window longitudinally disposed along a length of the second opposing blade, and further wherein the holding channel of the first opposing blade is positioned such that the ablation tool is aligned with the window of the second opposing blade in the second spaced apart position;

positioning the first and second opposing blades in the first spaced apart position;

placing the first and second opposing blades about tissue;

positioning the first and second opposing blades in the second spaced apart position such that the first and second opposing blades grasp the tissue;

forming a lesion in the tissue solely by the ablation tool; and assessing transmurality of the lesion formed by the ablation tool without removing the first and second opposing blades from the target tissue by visualizing the lesion formed by the ablation tool through the window in the second opposing blade.

13. A method of using an ablating device comprising:

providing an ablating device having first and second opposing blades moveable between a first spaced apart position and a second spaced apart position, wherein the first opposing blade includes an ablation tool disposed within a holding channel there within, and wherein the second opposing blade includes a window longitudinally disposed along a length of the second opposing blade and further wherein ablating device does not provide an ablation tool with the second opposing blade;

positioning the first and second opposing blades in the first spaced apart position;

placing the first and second opposing blades about tissue;

positioning the first and second opposing blades in the second spaced apart position such that the first and second opposing blades grasp the tissue;

forming a lesion in the tissue solely with the ablation tool of the first opposing blade; and assessing transmurality of the lesion formed by the ablation tool without removing the first and second opposing blades from the target tissue by visualizing the lesion formed by the ablation tool through the window in the second opposing blade.

* * * * *